(12) United States Patent
Sedic

(10) Patent No.: US 10,166,092 B2
(45) Date of Patent: Jan. 1, 2019

(54) TOOTHBRUSH WITH A CONTROLLED TRANSMISSION DIRECTION OF VIBRATION

(71) Applicant: Filip Sedic, Stockholm (SE)

(72) Inventor: Filip Sedic, Stockholm (SE)

(*) Notice: Subject to any disclaimer, the term of this patent is extended or adjusted under 35 U.S.C. 154(b) by 400 days.

(21) Appl. No.: 14/842,796

(22) Filed: Sep. 1, 2015

(65) Prior Publication Data
US 2017/0056145 A1    Mar. 2, 2017

(51) Int. Cl.
| | |
|---|---|
| A61C 17/34 | (2006.01) |
| A61H 13/00 | (2006.01) |
| A61C 17/22 | (2006.01) |
| A46B 9/04 | (2006.01) |

(52) U.S. Cl.
CPC ........ *A61C 17/3481* (2013.01); *A61C 17/225* (2013.01); *A61C 17/34* (2013.01); *A61H 13/00* (2013.01); *A46B 9/04* (2013.01); *A61C 17/221* (2013.01)

(58) Field of Classification Search
CPC . A61C 17/3481; A61C 17/221; A61C 17/225; A61C 17/34
USPC .......................................................... 15/188
See application file for complete search history.

(56) References Cited

U.S. PATENT DOCUMENTS

| | | | |
|---|---|---|---|
| 686,764 A | 11/1901 | Richards | |
| 1,817,585 A | 8/1931 | Samuel | |
| 2,225,331 A | 12/1940 | Campbell | |
| 2003/0046780 A1 | 3/2003 | Davis | |
| 2003/0172483 A1* | 9/2003 | Davis | A46B 5/0095 15/167.1 |
| 2009/0178215 A1 | 7/2009 | Gall et al. | |
| 2010/0269275 A1 | 10/2010 | Shimoyama et al. | |

(Continued)

FOREIGN PATENT DOCUMENTS

| | | |
|---|---|---|
| CN | 201070108 Y | 6/2008 |
| KR | 10-2012-0026955 A | 3/2012 |

(Continued)

OTHER PUBLICATIONS

Foreo, "Foreo Launches the ISSA mini, Designed to Care for the Future of Smiles," Aug. 2014, one page. [Online] [Retrieved Sep. 27, 2017] Retrieved from the Internet <URL:https://www.foreo.com/sites/default/files/field/file/press-articles/FOREO_ISSAmini_GlobalPR_EN_1.pdf.>.

(Continued)

*Primary Examiner* — Laura C Guidotti
(74) *Attorney, Agent, or Firm* — Fenwick & West LLP

(57) ABSTRACT

A toothbrush device includes one electric motor that provides the toothbrush with various frequencies of pulsations that are transmitted in a controlled fashion. The toothbrush device has a brush head with bristle touch-points, a handle, and a carrying case that extends from the head to the handle and holds the electric motor (e.g., a vibration motor). The electric motor generates vibration energy that travels through a shaft of the carrying case to the brush head in generally a single direction to vibrate the brush head. For example, the carrying case of the electric motor contacts the handle at a contact point, which is approximately at the center of the carrying case such that the majority of the vibrations generated by the electric motor are transmitted toward the brush head, while the vibrations towards other directions are minimized.

14 Claims, 6 Drawing Sheets

(56) References Cited

U.S. PATENT DOCUMENTS

2014/0259469 A1   9/2014   Garrigues et al.
2015/0173502 A1   6/2015   Sedic

FOREIGN PATENT DOCUMENTS

WO   WO 20051096882 A1   10/2005
WO   WO 2011/013533 A1   2/2011

OTHER PUBLICATIONS

State Intellectual Property Office of the People's Republic of China, First Office Action, Chinese Patent Application No. 201480068758.7, dated Feb. 4, 2017, thirteen pages.
AZO materials; Properties: Silicone Rubber, 2 pages, [online] [retrieved May 17, 2016], Retrieved from the internet <http://www.azom.com/properties.aspx?ArticleID=920>.
European Patent Office, Search Report and Opinion, European Patent Application No. 14872403.2, dated Jun. 21, 2017, seven pages.
PCT International Search Report and Written Opinion, PCT Application No. PCT/IB2016/002000, dated Jun. 30, 2017, fourteen pages.
Second Office Action for Chinese Patent Application No. CN 201480068758.7, dated Oct. 148, 2017, 8 pages.

* cited by examiner

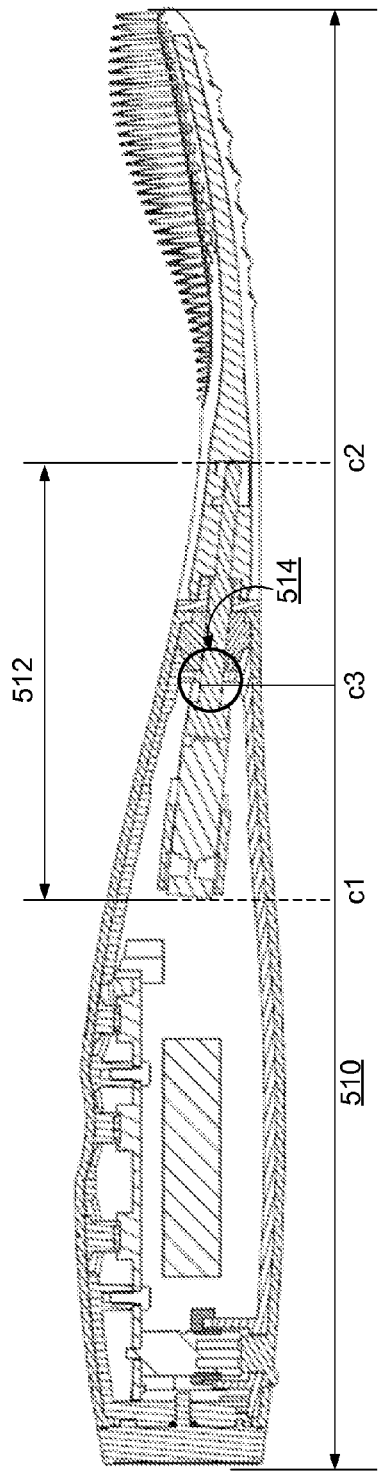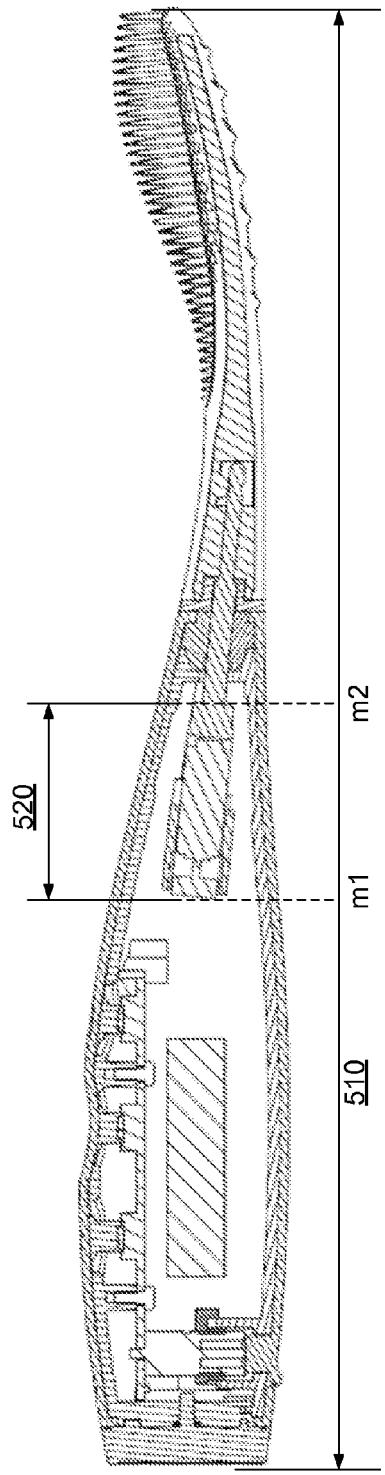

TOOTHBRUSH WITH A CONTROLLED TRANSMISSION DIRECTION OF VIBRATION

BACKGROUND

The disclosure relates generally to an electronic device, and more particularly to an electric toothbrush with a controlled transmission direction of vibration generated by one or more motors embedded in the electric toothbrush.

General mouth hygiene and oral health depends on effective removal of biofilm and food, which diminishes the presence of microbial cultures and excretions. Electric toothbrushes have become increasingly popular in the dental care and toothbrush market. A vibrating toothbrush head of an electric toothbrush combined with a manual toothbrush movement operated by a user can remove biofilm and other contaminates on teeth and gums for deep cleaning.

Existing designs of electric toothbrushes generally include a mechanical rotating toothbrush head having one or more vibration motors embedded in the handle of an electric toothbrush to provide mechanical energy to vibrate the toothbrush head (also referred to as vibration energy). The vibration motor can transmit the vibration energy in various transmission directions. Transmitting the vibration energy in various transmission directions results in several disadvantages, including loud noise and a poor feeling in a user's hand since strong oscillations from the vibration motor are transferred to the handle of the toothbrush. Moreover, cleaning performance may be greatly reduced since the vibration energy is distributed to not only toothbrush head, but also to other unwanted parts of the toothbrush in other transmission directions. Furthermore, existing designs of the electric toothbrushes require support for high power consumption due to the loss of vibration energy transmitted in uncontrolled transmission directions.

SUMMARY

Embodiments include a toothbrush device with at least one electric motor that provides the toothbrush with pulsations at one or more frequencies and the pulsations are transmitted to various parts of the toothbrush in a controlled fashion.

One embodiment of the toothbrush device is an electric toothbrush that includes a brush head with a plurality of bristle touch-points along rows and a handle connected to the head. The handle can include an outer protective cover surrounding the handle. The handle has an electric motor that can be contained or housed within (or otherwise connected to) a carrying case that suspends the motor within the handle. The electric motor is powered by an electronic circuitry (e.g., a printed circuit board or other controller and a battery), and is configured to generate vibration energy that vibrates the brush head.

The electric motor and its carrying case are located at determined positions within the handle of the toothbrush, where the determined positions enable the transmission of the vibrations generated by the electric motor in a controlled direction, e.g., with a majority of the vibrations going to the brush head and the remaining vibrations going anywhere other than the brush head being minimized. For example, in one embodiment, the contact point between the carrying case of the electric motor and the handle shell is held at a center position of the carrying case, where a solid shaft of the carrying case is configured to transmit the vibrations generated by the electric motor in a controlled direction towards the brush head. The center position of the contact point is defined with respect to the length of the carrying case. In another embodiment, the center position of the electric motor inside the device and within the hollow chamber of the carrying case is defined with respect to an overall length of the toothbrush device. The center position inside the hollow chamber of the carrying case can be further defined with respect to a position of the electronic circuitry within the handle of the toothbrush device.

Other embodiments include other types of electronic devices having one or more electric motors that generate oscillating pulsations, whose transmission is distributed along a controlled direction. Exemplary applications of the electronic device include an electric skin massager and a personal vibrator.

BRIEF DESCRIPTION OF THE DRAWINGS

FIG. 5A is a sectional view of an electric toothbrush having a carrying case of a vibration motor located in a determined location within the handle of the electric toothbrush according to one embodiment.

FIG. 5B is a sectional view of an electric toothbrush having a vibration motor located in a determined location within the handle of the electric toothbrush according to one embodiment.

The figures depict various embodiments of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Figure 1:
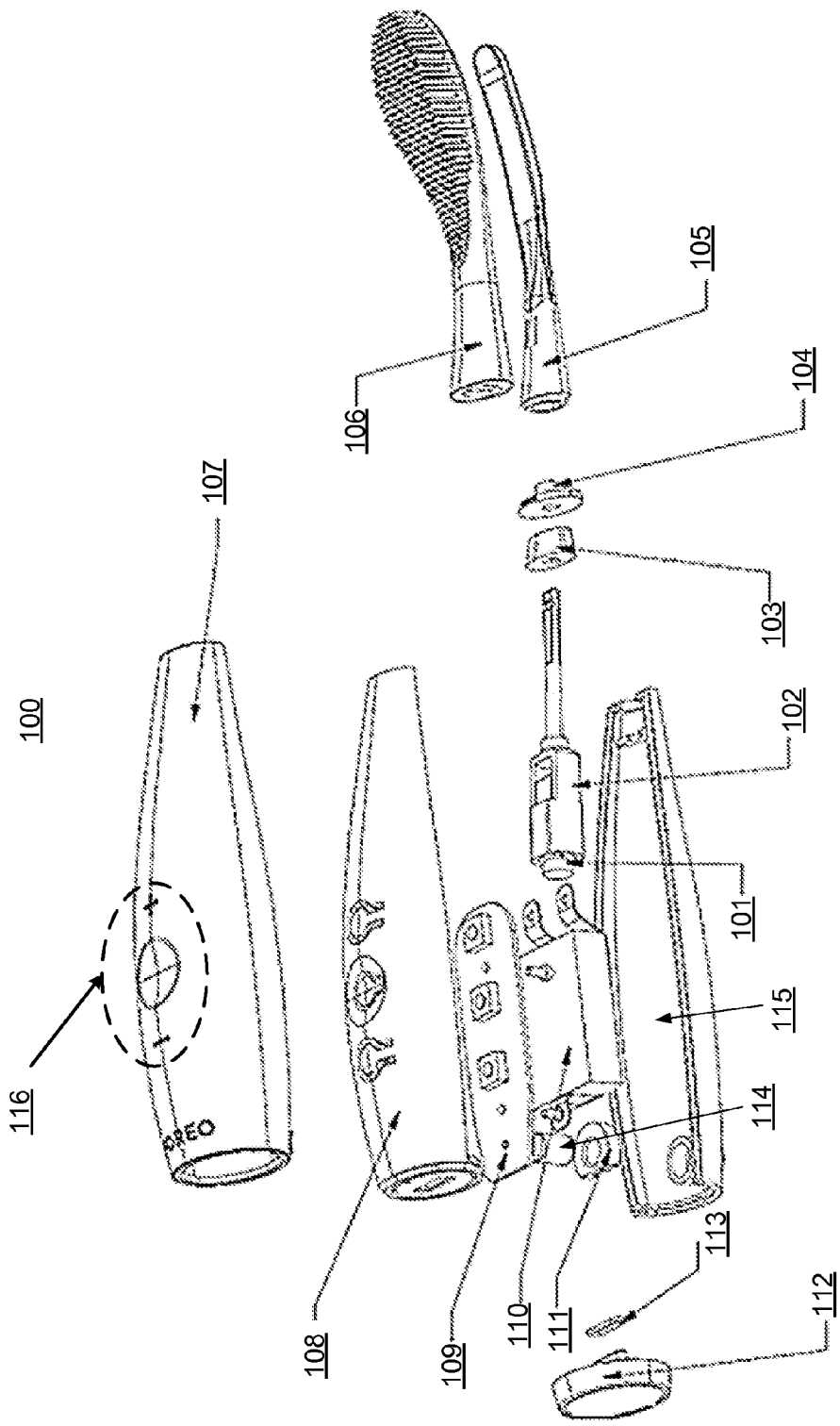
FIG. 1 is an exploded view of an electric toothbrush according to one embodiment.

FIG. 1 is an exploded view of an electric toothbrush 100 according to one embodiment. As shown in FIG. 1, the electric toothbrush 100 includes a vibration motor 101, a motor carrying case 102, a dampening portion 103, a decorative ring 104, a brush support 105, a brush head case 106, a handle case 107, an upper handle shell 108, an electronic board 109, a battery 110, a waterproof case of charging port 111, a base 112, a waterproof case of base 113, a connector or jack 114, a lower handle shell 115 and a user control 116. Other embodiments of the electric toothbrush 100 can have different, additional or less components. For example, the electric toothbrush 100 can have more than one vibration motor 101 in an alternative embodiment.

The vibration motor 101 generates vibration energy that vibrates the toothbrush 100. In one embodiment, the vibration motor 101 is a high-frequency and low-frequency oscillating motor. The high-frequency of the vibration motor 101 may provide oscillations between 50 and 300 Hz; the low-frequency of the vibration motor 101 provides oscillations in the 50-130 Hz range. The vibration motor 101 generates the oscillations (also referred to as vibrations) in an alternating fashion of high frequency and low frequency, which helps deep cleansing of the inner mouth surface or tissue and the stimulation of blood circulation and lymph flow within the mouth.

The vibration generated by the vibration motor 101 is transferred to the brush head, e.g., the brush support 105, through the motor carrying case 102. The brush support 105 is covered with a case, e.g., the brush head case 106, and transfers the vibration to the case 106, which drives the bristle on the case 106 to vibrate. The brush support 105 can be made of nylon, plastic, or other materials, and can form a rigid or bendable support for the brush head. The case 106 can be made of silicone or other materials. In some embodiments, it forms a skin or other form of covering over the entire brush head including the brush support 105 such that the head is completely encased in silicone with the brush support 105 inside the silicone case. In some cases, the connector that connects the brush head to the handle is not fully encased in silicone.

The bristles on the case 106 are arranged in a certain direction for providing biofilm removal from teeth. In one embodiment, the bristles are touch points arranged along rows, such as the bristle touch-points described in U.S. application Ser. No. 14/576,134, filed on Dec. 18, 2015, which is hereby incorporated by reference herein in its entirety. Each of the bristle touch-points is a single solid elongate structure and is composed of a polymer material. For example, where the case 106 is a silicone case, the bristle touch-points can be integral to this case and can be part of a single molded piece of silicone skin that covers the brush head.

The vibration motor 101 and the motor carrying case can be located in the electric toothbrush 100 in their corresponding determined positions such that the vibration energy generated by the vibration motor 101 is transmitted in a controlled direction, e.g., towards the toothbrush head while the vibration energy distributed to other parts of the electric toothbrush 100 are minimized. Various embodiments for positioning of the motor carrying case 102 and the vibration motor 101 within the electric toothbrush 100 are further described below with reference to FIG. 4 and FIGS. 5A-5B.

In one embodiment, the vibration motor 101 is powered by a battery, e.g., the battery 110, or other electronic circuitry (e.g., a controller) presented on a printed circuit board, e.g., the electronic board 109, coupled with the charging port 111. The jack 114 can be a DC or other type of jack. It also can couple to the vibration motor 101 to provide electrical power to the vibration motor 101. The battery 110 provides electronic energy for the vibration motor 101. The battery 110 is charged by the charger port 111, which enables various charging means, such as using alternating current (AC) means, transformer or power converters, inductive charging, or any other suitable charging means. The battery 110 can also be charged by a base 112 protected by a waterproof case of base 113, for example, via inductive charging based on a transmitting coil in the base 112 and a receiving coil in the electric toothbrush 100 or via metal contacts in the base 112 and the electric toothbrush 100. In other embodiments, the toothbrush instead has a replaceable battery and is not rechargeable.

The electronic board 109 is used to turn on/off the electric toothbrush 100, and to increase or decrease the power applied to the vibration motor 101. It also can be used to indicate the charging status of the battery 110 using a light indicator. For example, if the electric toothbrush 100 is out of battery charge, the light indicator flashes and/or changes color to red. If the charging is completed, the light indicator stops flashing and/or changes color to green.

A top covering, e.g., the handle case 107, upper casing, e.g., the upper handle shell 108, lower casing, e.g., the lower handle shell 115, a base 112, and a waterproof case of base 113, together form an outer protective cover for the handle of the electric toothbrush 100. In some embodiments, the outer protective cover includes fewer of these components. For example, it might not include a base 112 or waterproof case of the base 113, or it might not include an upper casing, or the handle shell might be a single piece or have more than an upper and lower shell. In one embodiment, the upper handle shell 108 and lower handle shell 115 are made of plastic or other suitable materials. The handle case 107 can be made of silicone. In some embodiments, like the brush head, the handle includes a silicone skin or other form a silicon covering that encases most of the handle.

The handle can also include one or more user controls, e.g., user control 116 shown in FIG. 1, that interact with the internal components, such as the electronic board 109, to control vibration of the toothbrush, and these user controls can sit under and be operated through the silicone skin formed by the handle case 107. For example, the embodiment of FIG. 1 includes a "+" and a "−" sign that can increase or decrease the vibrations, respectively. A button in the middle can be operated by the user's finger or thumb to turn on or off the vibrations, or to change between different vibration settings or patterns of vibration. These user controls can be protected from water damage during use of the toothbrush by the silicone covering of the head.

In some embodiments, the base 112 is a clear base, composed of plastic, glass, or other suitable materials. This base can light up when the device is on, when it is charging, when it is changing vibration settings, when it is time for the user to switch to brushing a different quadrant of the mount, or to indicate other changes with the toothbrush operation.

In one embodiment, the vibration motor 101 is attached to the motor carrying case 102, which holds the vibration motor 101. The motor carrying case 102 is coupled to the upper handle shell 108. The motor carrying case 102 is connected with the brush 105 through the dampening portion 103 that is positioned around the motor carrying case fastened by the decorative ring 104. The decorative ring 104 can be composed of plastic, metal or other suitable materials. The dampening portion 103 can be composed of silicone or other suitable materials. It assists in the dampening of vibration to the handle, and thus the focusing of vibration into the shaft or rod of the motor carrying case 102 that is positioned within the head.

Figure 2:
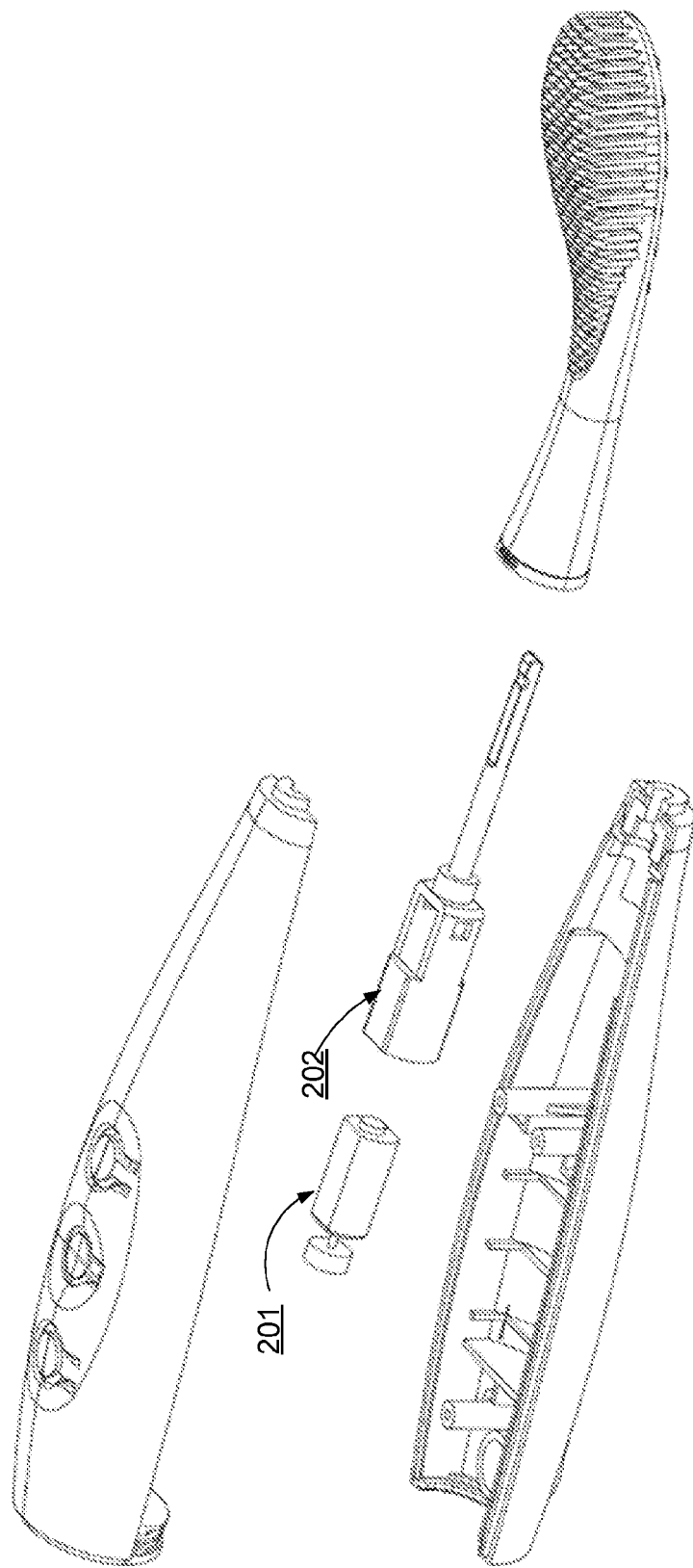
FIG. 2 is a perspective view of a vibration motor and a motor carrying case of the electric toothbrush illustrated in FIG. 1 according to one embodiment.

FIG. 2 shows a perspective view of the toothbrush, illustrating the vibration motor and its corresponding motor carrying case. These can be the vibration motor 101 and motor carrying case 102 of FIG. 1 or can be a different embodiment. As shown in FIG. 2, the vibration motor 201 (corresponding to the vibration motor 101 in FIG. 1) is separated from the motor carrying case 202 (corresponding to the vibration motor 102 in FIG. 1). The vibration motor 201 is inserted into an opening of and fixed on the motor carrying case 202.

Figure 3:
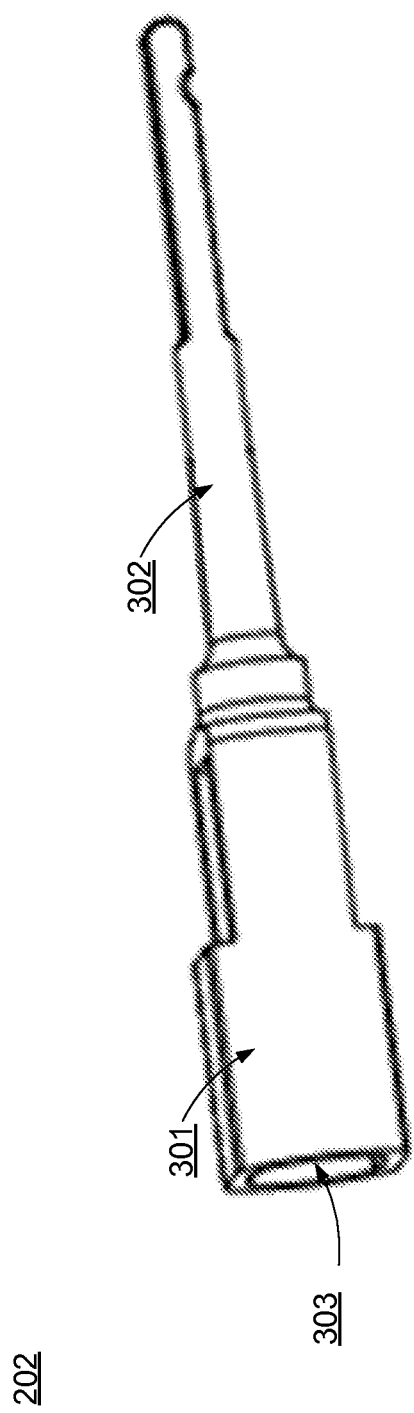
FIG. 3 is a side view of the motor carrying case of the electric toothbrush illustrated in FIG. 2 according to one embodiment.

FIG. 3 is a side view of the motor carrying case of the electric toothbrush according to one embodiment. This can be the motor carrying case 202 of FIG. 2 or 101 of FIG. 3, or can be a different embodiment. As shown in FIG. 3, the motor carrying case 202 has a body 301 with an opening 303 to a hollow chamber inside and a solid shaft 302. The hollow chamber 303 is used to hold the vibration motor 201 or 101 within the body 301 of the motor carrying case 202. The solid shaft 302 is a solid elongated structure for transferring the vibration energy generated by the vibration motor 201 to the brush support 105. The solid shaft 302 runs through two connectors, e.g., the dampening portion 103 and the decorative ring 104 that each have openings through which the solid shaft 302 can be positioned and that each form a ring around the solid shaft 302. The dampening portion 103 sits between the decorative ring 104 and the portion of the motor carrying case 202 that extends into and is suspended within the handle. The dampening portion 103 acts to dampen or reduce the vibrations transmitted from the motor carrying case 202 to the handle. In one embodiment, the dampening portion 103 wraps around a portion of the solid shaft 302 as it exits the handle into the brush head such that either none of the solid shaft 302 (and none of the motor carrying case 202) contacts the handle case. In another embodiment, the dampening portion 103 wraps around a portion of the solid shaft 302 as it exits the handle into the brush head such that the solid shaft 302 only contacts the handle case or handle shells at one point, just as it exits the handle.

Figure 4:
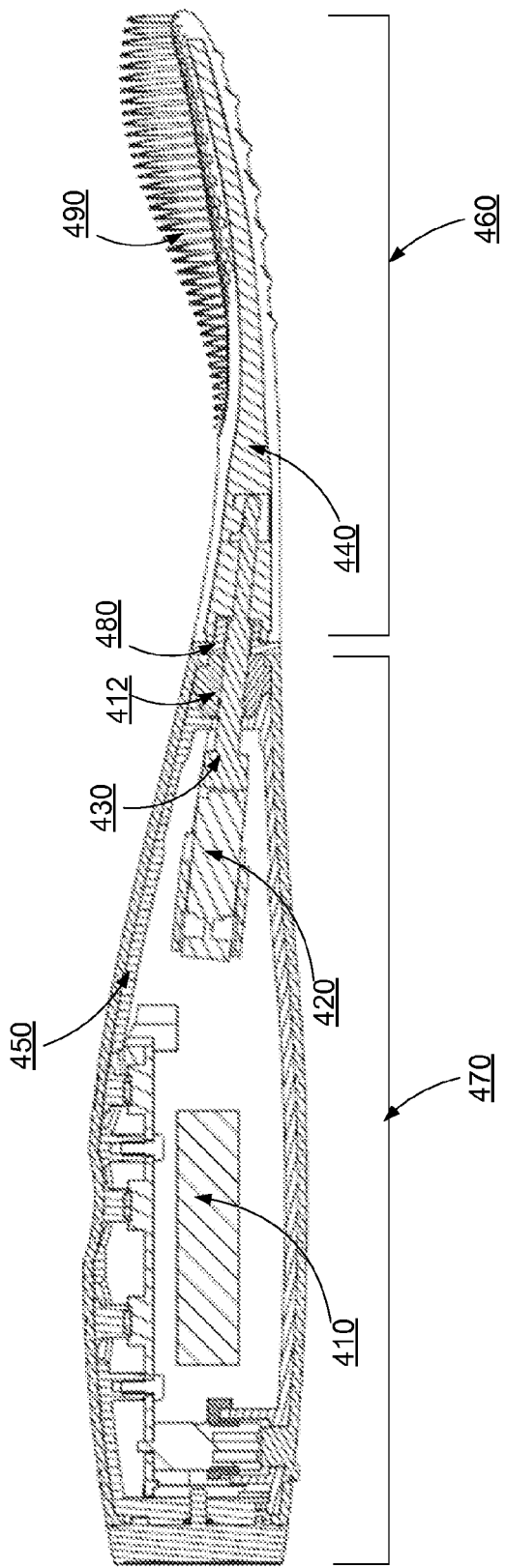
FIG. 4 is a sectional view of the electric toothbrush illustrated in FIG. 1 showing connections of the vibration motor embedded in the electric toothbrush according to one embodiment.

Turning now to FIG. 4, FIG. 4 is a sectional view of the electric toothbrush showing connections of the vibration motor 420 (corresponding to vibration motor 101) embedded in the electric toothbrush, such as in toothbrush 100 of FIG. 1 according to one embodiment. As shown in FIG. 4, the electric toothbrush 100 has a head portion 460 and a handle portion 470, which are connected by a decorative ring 480 (corresponding to the decorative ring 104 in FIG. 1). The head can be detached from the handle portion at the location of the decorative ring 480. A vibration motor 420 (corresponding to the vibration motor 101 in FIG. 1) is embedded in the hollow cavity of a motor carrying case 430 (corresponding to the motor carrying case 102 in FIG. 1) within the handle portion 470. In one embodiment, the vibration motor 420 powered by the battery 410 provides a type of motion to the brush support 440, such as vertical tapping, rotating or translational motion, through the motor carrying case 430. The brush support 440 transfers the motion to the silicone case 490 (corresponding to the brush support 105 in FIG. 1), and drive the bristle on the silicone case 490 to clean various parts of the mouth (e.g., teeth, gums, tongue, inner cheek tissue, and the like).

In one embodiment, a part of the solid shaft of the motor carrying case 430 is coupled to one end of the vibration motor 420 toward the head portion 460 is connected to a handle shell 450; the remaining part of the solid shaft of the motor carrying case 430 is directly connected to a brush support 440 (corresponding to the brush support 105 in FIG. 1). The other end of the vibration motor 420 is connected via electrodes or wires (not shown in FIG. 4) to a battery 410 (corresponding to the battery 110 in FIG. 1).

As shown in FIG. 4, the body of the vibration motor 420 is detached from the handle shell 450. Only one end of the motor carrying case holding the vibration motor 420 is physically attached to the electric toothbrush 100, e.g., through the decorative ring 480 and silicone portion to the brush support 440. In other words, the vibration motor plus motor carrying case is completely detached or is almost completely detached from the handle case 107 and handle shells 108, 115, and it generally floats inside the handle. It connects to the brush support 440 via the solid shaft, and has zero or minimal contact with the handle to avoid transmitting vibrations to the handle. A first portion of the shaft is positioned within the head. The handle surrounds the body 301 and a second portion of the shaft 302 of the motor carrying case. The shaft thus runs through the dampening portion 412 and decorative ring 480, exiting the handle and entering the head. FIG. 4 shows that the body of the carrying case (the part holding the motor) is suspended within and does not contact the handle. A majority of the vibrations (e.g., at least 99%, 98%, 97%, 96%, 95%, 90%, 85%, 80%, 75% and so forth of the total amount vibration caused by the motor) is transmitted to the brush head rather than to the handle.

Detaching the vibration motor 420 from the handle shell 450 provides a variety of benefits. For example, during the operation of the electric toothbrush 100, the oscillations generated by the vibration motor 420 that are transferred from the vibration motor 420 to the battery 410 are negligible because of the detachment of the vibration motor 420 from the handle shell 450 and a determined distance between the battery 410 and the vibration motor 420. In one embodiment, the vibration motor 420 is at a distance greater than a threshold distance from the battery 410. For example, the distance of the battery from the motor might be 4 centimeters (cm), 3 cm, 2 cm, or some other distance. The threshold distance is configurable depending on a variety of factors, e.g., an overall length of the electric toothbrush 100, the relative lengths among the handle portion 470, the vibration motor 420, and the head portion 460 of the electric toothbrush 100. In some embodiments, the threshold distance might be at least some number such as at least 3 cm apart.

On the other end of the vibration motor 420, the vibration transferred from the motor carrying case 430 to the handle shell 450 can also be significantly reduced by the dampening portion 412 (corresponding to the dampening portion 103 in FIG. 1), which separates the motor carrying case 430 and the handle shell 450. Thus, the vibration generated by the vibration motor 420 cannot be transmitted to the handle shell 450 directly, thereby the variation on the handle portion 470 is weakened and the user experience with the handle of the electric toothbrush is improved.

To further enhance the user experience with the electric toothbrush 100 shown in FIG. 1 or any of the other figures, the motor carrying case 102 and the vibration motor 101 can be located in the electric toothbrush 100 in determined positions such that the vibration energy generated by the vibration motor 101 can be transmitted in a controlled direction, e.g., towards the toothbrush head while the vibration energy distributed to other parts of the electric toothbrush 100 is minimized. FIG. 5A and FIG. 5B illustrate exemplary embodiments of positioning the motor carrying case and the vibration motor 101, respectively, within the electric toothbrush 100 to control the transmission of the vibration generated by the vibration motor 101.

FIG. 5A is a sectional view of an electric toothbrush having a carrying case of a vibration motor located in a determined location within the handle of the electric toothbrush according to one embodiment. As shown in FIG. 5A, the electric toothbrush has an overall length 510 (e.g., 20 cm) and the motor carrying case 430 has an overall length 512 (e.g., 6 cm) defined by two anchor positions: c1 and c2. The motor carrying case 430 is positioned inside the handle, where the shaft portion of the carrying case contacts the handle shell 450 at a contact point 514. In the embodiment shown in FIG. 5A, the contact point 514 between the motor carrying case 430 and the handle shell 450 corresponds to a position, c3, with respect to the overall length 512 of the motor carrying case 430, where the position c3 is approximately at the center of the overall length 512 of the motor carrying case 430.

FIG. 5B is a sectional view of an electric toothbrush having a vibration motor located in a determined location within the handle of the electric toothbrush according to one embodiment. As shown in FIG. 5B, the electric toothbrush has an overall length 510 (e.g., 20 cm) and the part of the vibration motor that is not connected to the electric toothbrush has a length 520 (e.g., 2 cm). The vibration motor is located around the center of the electric toothbrush, and the center position is defined by two anchor positions, m1 and m2.

Combined with connections shown in FIG. 4, positioning the motor carrying case with a contact point between the motor carrying case and the handle shell in the center of the motor carrying case enables the transmission of most of the vibration generated by the vibration motor 420 along one transmission direction toward to the brush support 440. The vibration energy is provided to the brush head with high concentration, and cleaning performance is enhanced. An additional benefit includes reduced power consumption by the vibration motor because a smaller vibration motor in terms of amount of electrical power needed can be used to generate the same amount of vibration.

Figure 6:
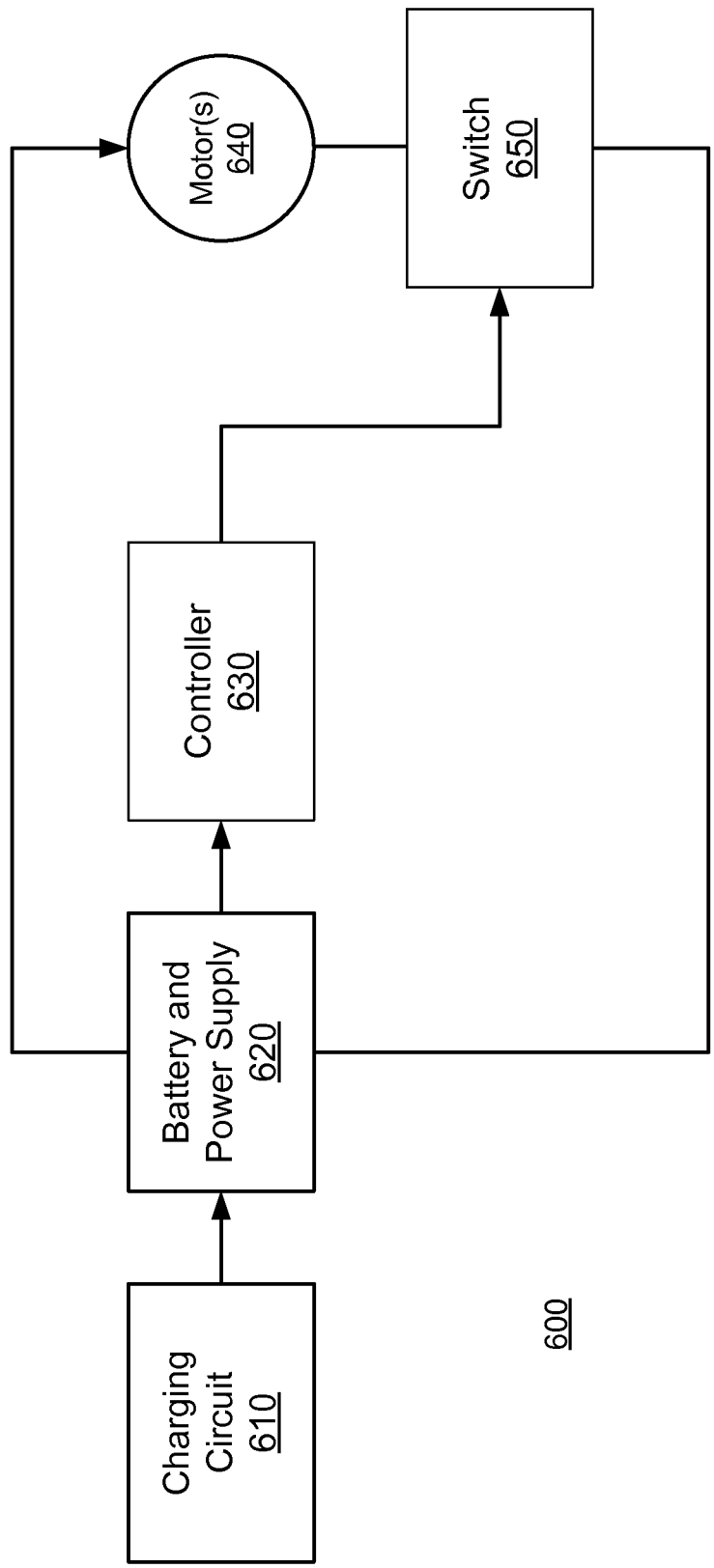
FIG. 6 is a graphical illustration of internal components of an electronic device having one or more electric motors according to one embodiment.

FIG. 6 is a graphical illustration of internal components of an electronic device 600 having one or more electric motors according to one embodiment. In one embodiment shown in FIG. 6, the electronic device 600 has a charging circuit 610, a battery and power supply 620, a controller 630, one or more electric motors 640 and a switch 650. The charging circuit 610 charges the battery and power supply 620, which provides electric power to the electric motor(s) 640. The controller 630 enables or disables power supply from the battery 620 to the electric motor(s) 640 via actuation of the switch 650 in pulses of specified pulse duration period based on levels of the power supply voltage, thereby controlling the rotational operation of the electric motor(s) 640. An example of the electronic device 600 is an electric toothbrush 100 illustrated in FIG. 1. Other examples of the electronic device 600 include any electronic device that has one or more electric motors to generate vibrations, whose transition has a controlled direction, such as skin massagers, eye massagers, back massagers, personal vibrators, and other types of vibrating devices.

SUMMARY

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

What is claimed is:

1. An electronic device comprising:
   a toothbrush head comprising a plurality of bristle touch-points arranged along rows, each of the plurality of the bristle touch-points being a single solid elongate structure extending from the toothbrush head and comprising a polymer material;
   a carrying case comprising a body and a shaft, a first portion of the shaft being positioned within the toothbrush head;
   electronic circuitry;
   a handle comprising a handle shell surrounding the electronic circuitry, the body, and a second portion of the shaft of the carrying case, the body of the carrying case suspended within and not contacting the handle and only physically coupled at a first region to a dampener positioned between the second portion of the shaft and the handle shell, the shaft of the carrying case extending from the handle and into the toothbrush head; and
   an electric motor connected to and positioned within the body of the carrying case such that the electric motor within the carrying case is suspended within the handle, the electric motor electrically coupled to the electronic circuitry and configured to generate vibration energy that is transmitted to the toothbrush head through the shaft of the carrying case to vibrate the toothbrush head.

2. The electronic device of claim 1, wherein the electric motor is a vibration motor and the electronic circuitry comprises a battery, wherein the carrying case is indirectly coupled to the battery by way of the electric motor retained within the carrying case.

3. The electronic device of claim 2, wherein the electric motor is vibrationally isolated from and physically displaced from the battery and coupled to the battery by a set of wires.

4. The electronic device of claim 1, wherein the polymer material is silicone.

5. The electronic device of claim 1, wherein the electric motor is a high-frequency and a low-frequency oscillating motor.

6. The electronic device of claim 1, wherein the carrying case further comprises a hollow chamber that holds the electric motor within the carrying case such that the electric motor is suspended within the handle.

7. The electronic device of claim 1, wherein the dampener positioned between the second portion of the shaft and the handle shell comprises a silicone material.

8. The electronic device of claim 1, wherein the shaft is a solid, physically continuous elongated shaft that extends from the body in the handle and into the rigid brush support.

9. The electronic device of claim 8, wherein the controlled direction of the transmission of the vibrations enables the shaft to transmit a majority of the vibrations towards the toothbrush head rather than towards the handle.

10. The electronic device of claim 1, wherein the shaft contacts the dampener at a contact point approximately at the center of the carrying case as defined with respect to an overall length of the carrying case.

11. The electronic device of claim 1, wherein the electronic motor is located approximately at the center of the toothbrush device as defined with respect to an overall length of the toothbrush device.

12. The electronic device of claim 1, wherein the handle shell comprises an upper and lower shell of the handle and a silicon covering over the handle.

13. The electronic device of claim 1, further comprising:
   a rigid brush support comprising a stem with an exterior surface; and
   a continuum of compliant polymer material coupled to a majority of the exterior surface of the stem and encasing the stem of the rigid brush support, wherein the continuum defines the toothbrush head;

wherein the first portion of the shaft of the carrying case is directly coupled to the rigid brush support and physically displaced from the continuum of compliant material by the rigid brush support, the rigid brush support transferring vibration from the shaft to the continuum of compliant material during operation of the electronic device, and wherein the electric motor is electrically coupled to the electronic circuitry and configured to generate vibration energy that is transmitted to the toothbrush head through the shaft of the carrying case, to the rigid brush support, to the continuum, to vibrate the toothbrush head.

14. An electronic device comprising:

a toothbrush head comprising a plurality of bristle touchpoints arranged along rows;

a carrying case comprising a body and a shaft, a first portion of the shaft being positioned within the toothbrush head; and a handle comprising a handle shell surrounding the body and a second portion of the shaft of the carrying case, the body of the carrying case suspended within the handle and only physically coupled at a first region to a dampener positioned between the second portion of the shaft and the handle shell, the shaft of the carrying case extending from the handle and into the toothbrush head; and an electric motor connected to the body of the carrying case such that the electric motor is suspended within the handle, the electric motor electrically coupled to the electronic circuitry and configured to generate vibration energy that is transmitted to the toothbrush head through the shaft of the carrying case to vibrate the toothbrush head.

\* \* \* \* \*

UNITED STATES PATENT AND TRADEMARK OFFICE
CERTIFICATE OF CORRECTION

PATENT NO. : 10,166,092 B2
APPLICATION NO. : 14/842796
DATED : January 1, 2019
INVENTOR(S) : Filip Sedic Page 1 of 1

It is certified that error appears in the above-identified patent and that said Letters Patent is hereby corrected as shown below:

In the Claims

Column 8, Lines 35-37, replace "electric motor is a high-frequency and a low-frequency oscillating motor" with --electric motor is a high-frequency or a low-frequency oscillating motor--

Column 10, Lines 14-15, replace "coupled to the electronic circuitry" with --coupled to electronic circuitry--

Signed and Sealed this
Fifth Day of November, 2019

Andrei Iancu
*Director of the United States Patent and Trademark Office*